United States Patent [19]

VanZandt et al.

[11] Patent Number: 5,364,185
[45] Date of Patent: Nov. 15, 1994

[54] HIGH PERFORMANCE MINIATURE HYGROMETER AND METHOD THEREOF

[75] Inventors: Thomas R. VanZandt, Redondo Beach; William J. Kaiser, West Covina; Thomas W. Kenny, Glendale; David Crisp, Durate, all of Calif.

[73] Assignee: California Institute of Technology, Pasadena, Calif.

[21] Appl. No.: 46,760

[22] Filed: Apr. 16, 1993

[51] Int. Cl.$^5$ ...................... G01N 25/68; G01N 25/02
[52] U.S. Cl. ..................................... 374/28; 73/29.02
[58] Field of Search ......................... 374/28; 73/29.02

[56] References Cited

U.S. PATENT DOCUMENTS

| | | | |
|---|---|---|---|
| 4,378,168 | 3/1983 | Kuisma et al. | 374/28 |
| 4,589,274 | 5/1986 | Boyle et al. | 374/28 |
| 4,626,774 | 12/1986 | Regtien | 374/28 |
| 4,877,329 | 10/1989 | Sauerbaum et al. | 374/28 |
| 4,898,476 | 2/1990 | Herrmann et al. | 374/28 |
| 4,948,263 | 8/1990 | Herrmann et al. | 374/28 |

FOREIGN PATENT DOCUMENTS

| | | | |
|---|---|---|---|
| 0282900 | 9/1988 | European Pat. Off. | 374/28 |
| 3446277 | 6/1986 | Germany | 374/28 |
| 0075388 | 6/1977 | Japan | 374/28 |
| 2126350 | 3/1984 | United Kingdom | 374/28 |
| 1495701 | 7/1989 | U.S.S.R. | 374/28 |
| 1711057 | 2/1992 | U.S.S.R. | 73/29.02 |

OTHER PUBLICATIONS

Hygrometery by H. Spencer-Gregory and E. Rourke, published by Pitman Publishing Company.

Primary Examiner—Diego F. F. Gutierrez
Attorney, Agent, or Firm—Leonard Tachner

[57] ABSTRACT

An uncoated interdigitated transducer is cooled from a temperature above the dew point to a temperature below the dew point, while a parameter of a signal of the transducer is measured. The reduction in temperature causes a monotonic change in transducer signal because that signal is sensitive primarily to the water loading of the transducer surface as water forms on that surface due to the reduction in temperature. As the dew point is approached with temperature reduction, the slope of the curve of transducer signal with respect to temperature, remains relatively constant. However, as the dew point is reached the slope of that curve increases and because of changes in the structure of the water layer on the surface of the transducer, at the dew point the transducer responds with a clear shift in the rate at which the transducer signal changes. The temperature at which the second derivative of signal vs. temperature peaks can be readily used to identify with extreme accuracy, the precise dew point. The measurement technique employed by the present invention is relatively immune to surface contamination which remains significantly unchanged during the brief measurement period.

6 Claims, 3 Drawing Sheets

HIGH PERFORMANCE MINIATURE HYGROMETER AND METHOD THEREOF

ORIGIN OF INVENTION

The invention described herein was made in the performance of work under a NASA contract, and is subject to the provisions of Public Law 96-517 (35 USC 202) in which the Contractor has elected to retain title.

TECHNICAL FIELD

The present invention relates generally to the field of hygrometry and more specifically to a miniature, solid state hygrometer in which the signal from an interdigitated transducer (IDT)-based moisture sensor is monitored while temperature is decreased from a point above dew point to a point below dew point. Structural characteristics of water forming on the moisture transducer surface at dew point produce an abrupt change in signal which can be unamibiguously observed by monitoring the second derivative of signal versus temperature.

BACKGROUND ART

The accurate measurement of humidity is crucial to a number of diverse fields, including meteorology, materials processing and manufacturing and environmental control (HVAC). These applications require measurement over a very wide range of water vapor concentrations (greater than 1% to less than 1 part per million by volume), over a large range of ambient temperatures (170 degrees K. to 500 degrees K.). Presently, instruments which accurately measure water vapor concentration typically use optical techniques consisting of optical absorption and optical detection of dew point. Of these techniques, optical dew point detection is normally favored in cases where extreme accuracy and reproducability are required. For example, so called "chilled mirror" dew point hygrometers are often used as reference sensors for calibration. Unfortunately, these instruments are large, complex and expensive. This precludes their use in a large number of important applications. As an alternative, many approaches for microsensor-based humidity measurement have been explored. These include a variety of solid state sensors which generally measure the effect of water on the electrical properties of some material. These microsensors have a number of drawbacks, including poor sensitivity, large hysteresis, limited operating range and significant aging effects.

Accordingly, a miniature hygrometer, with the inherent accuracy and reproducability of optical dew point hygrometers is needed for a number of applications. Such sensors must be able to measure water vapor over a wide range of concentrations in widely varying ambient environments. Past efforts of developing solid state microsensors have not been entirely successful. Typically, these sensors require exotic solid state materials in order to achieve the required sensitivity.

Specifically, the normal electronic transduction mechanisms are not sensitive enough for efficient operation. In order to overcome this, most microsensors use a variety of hygroscopic materials to increase water uptake in the sensor. This approach is unattractive because it leads to a number of errors, including non-linearity, hysteresis, temperature sensitivity and aging effects. As a result, these miniature sensors are not suitable for situations in which high accuracy and reproducability are needed in diverse operating conditions.

Dew point detection provides a way of accurately measuring water vapor content. Unfortunately, current dew point sensors employ inefficient transducers for water vapor detection. Such devices use a chilled mirror in conjunction with an optical reflectance transducer to measure the condensation of moisture at the dew point temperature. The optical transducers presently used are both bulky and slow. In addition, they require relatively complex electronics. The result is that current dew point hygrometers are large, slow and complicated devices. The performance of current dew point sensors also suffers from the fact that they are sensitive to contamination (e.g., dust loading of the mirror surface). This limitation relates to the actual measurement algorithm used in the device: the moisture transducer's surface temperature is feedback controlled to stay at dewpoint. Because of this, unwanted shifts in moisture transducer output due to its inherent instabilities lead to errors in measured dewpoint. Presently, this feedback technique is used primarily to offset the limited speed of the sensor. Improving the speed of the moisture transducer and reducing its size would allow a new measurement algorithm to be used. A new approach is therefore needed to allow miniaturization of its device.

One dew point detection device that is relevant to the present invention is described in U.S. Pat. No. 4,378,168 issued Mar. 29, 1983 to Kuisma et al. This prior art dew point detection device comprises a piezo-electric sensor having a material for transmitting acoustic waves along a surface that is subjected to the condensation and presence of dew and liquid to be detected. A wave inducing device includes a transmitter for producing an acoustic surface wave on the surface in conjunction with piezoelectric phenomena of the sensor. A detector includes a receiver for receiving the wave after transmission thereof, across the surface of the device. The wave is variably attenuated in transmission between the transmitter and the receiver in accordance with the dew or liquid on the surface and a measurement device measures the attenuation of the detected wave and thereby indicates the dew point or presence on the surface. Unfortunately, the method and apparatus disclosed in the Kuisma et al patent, does not address a major problem in current instruments, namely contamination-based errors. More specifically, in the apparatus described in the aforementioned prior art patent, the stability of the surface acoustic wave dew point sensor is required for accurate measurement. Such stability is required because a control loop is being used to hold a parameter of the surface acoustic wave sensor, such as attenuation or impedance, fixed. Because of this, drifts in the dew sensor will lead to errors in dew point. Thus, despite the disclosure in the Kuisma et al patent, the need for a miniaturized hygrometer, capable of measuring dew point with extreme accuracy, remains an unfilled need.

STATEMENT OF THE INVENTION

The present invention comprises a new dew point hygrometer that varies from current chilled mirror instruments in two respects. First, it uses IDTs to detect water vapor. These transducers may be used to drive surface resonators or they may be used as passive capacitive moisture sensors. Each of these approaches is sensitive to water loading. Secondly, this new hygrometer uses a parametric approach of dew point detection in which a change in transducer output is measured as a function of a specific thermodynamic quantity. Consequently, in the present invention, the transducer is required to measure only relative quantities, thereby rendering the performance thereof, largely immune from shifts in the response of the moisture transducer. In the present invention, an uncoated IDT is cooled from a temperature above the dew point to a temperature below the dew point, while the moisture-dependent signal from the sensor is measured. The reduction in temperature causes a monotonic change in sensor signal, because that signal is sensitive primarily to the water loading of the sensor surface as water forms on that surface due to the reduction in temperature. As the dew point is approached with temperature reduction, the slope of the curve of sensor signal with temperature, remains relatively constant. However, as the dew point is reached the slope of that curve increases and because of changes in the structure of the water layer on the surface of the sensor, at the dew point the sensor responds with a clear shift in the rate at which the moisture sensor output change. The temperature at which the slope change peaks thus gives an unambiguous measure of dew point. In fact, determining the second derivative of moisture signal vs. temperature allows this effect to be clearly seen as a peak at the dew point temperature which can be readily used to identify with extreme accuracy, the precise dew point. However, equally important is the fact that the parameter used to determine dew point in the present invention is not an absolute parameter, such as for example, the attenuation of surface wave magnitude in the aforementioned prior art patent. Consequently, the measurement technique employed by the present invention is relatively immune to surface contamination, thereby overcoming a significant disadvantage of the aforementioned prior art.

Thus, the present invention may be readily implemented by employing an uncoated IDT positioned on a heater/cooler apparatus for controlled variation of the sensor temperature. A temperature sensor may be integrated with the IDT to accurately measure its temperature. The relevant IDT signal and temperature may be monitored simultaneously. Well known electronic devices may be used to control the temperature of the heater/cooler in a precisely predetermined fashion, while IDT temperature and signal are measured, so that the IDT output can be determined as a function of temperature. A second derivative of that function may be used to produce a clear and unambiguous indication of the dew point adjacent to the IDT surface. The entire sensor occupies a volume of less than four cubic inches and measures dew point depressions of up to 100 degrees Centigrade from ambient with an accuracy of 0.1 degrees Centigrade, with a significant improvement in the measurement speed as compared to chilled mirror instruments.

OBJECTS OF THE INVENTION

It is therefore a principal object of the present invention to provide an improved miniature hygrometer of the type which employs an IDT-based moisture sensor to measure dew point, but wherein dew point measurement is made relatively insensitive to surface contamination-based errors which affect the stability of conventional moisture wave sensors and thus the measurement accuracy of prior art devices.

It is another object of the present invention to provide a miniature hygrometer with the inherent accuracy and reproducability of optical dew point hygrometers, but with a significant reduction in sensor volume and a significant increase in measurement speed.

It is still an additional object of the present invention to provide an IDT-based hygrometer based on the variation in IDT sensor signal vs. temperature in the region of dew point, as opposed to measurement of an absolute quantity related to sensor performance.

BRIEF DESCRIPTION OF THE DRAWINGS

The aforementioned objects and advantages of the present invention, as well as additional objects and advantages thereof will be more fully understood hereinafter as a result of a detailed description of a preferred embodiment when taken in conjunction with the following drawings in which.

DETAILED DESCRIPTION OF A PREFERRED EMBODIMENT

Figure 1:
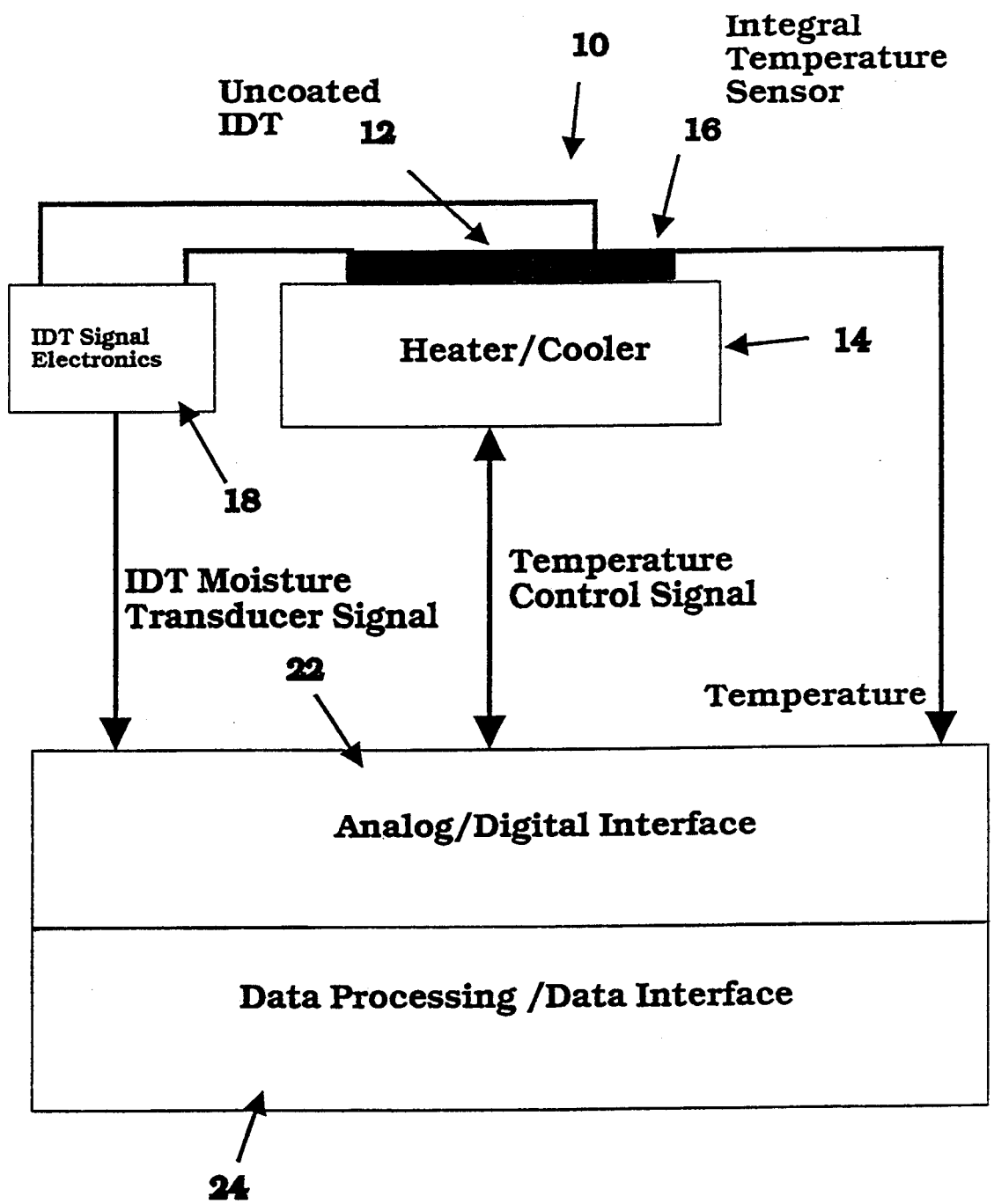
FIG. 1 is a block diagram of a preferred embodiment of the invention.

Referring first to FIG. 1, it will be seen that a hygrometer 10 of the present invention comprises an uncoated IDT 12 mounted on a heater/cooler 14 and integrated with a temperature sensor 16. Interdigitated transducers (IDT) are composed of closely spaced pairs of electrodes on an insulating substrate. These devices can be used for moisture detection in a number of modes. The general structure can be used as a passive electrical impedance (capacitive) whose value is strongly dependent on water loading. In this case, the dielectric constant associated with an adsorbed water layer leads to a large increase in capacitance. Alternatively, if the substrate is piezoelectric (e.g., quartz), the electrodes can be used to generate and receive surface acoustic waves. This allows the formation of acoustic delay lines and resonators which are sensitive to moisture through the strong interaction of the surface wave with an adsorbed water layer. In the case of a surface acoustic wave resonator, the device's resonant frequency is dependent on water loading: adsorbed water leads to a reduction in resonator frequency.

In the present invention, the signal from the IDT moisture sensor is measured with the appropriate signal conditioning electronics 18. As seen further in FIG. 1, the present invention comprises an analog/digital interface 22 and a data processing/data interface 24. Interface 22 receives analog signals indicative of IDT signal and temperature, and provides an analog output signal which controls temperature at the IDT sensor 12 by adjusting the heater/cooler 14 to vary the temperature in a predetermined manner, such as from a point above the dew point temperature to below the dew point temperature during a dew point measurement. Interface 22 also provides means for converting the input analog signals corresponding to the IDT signal and temperature to digital representations thereof and also for providing digital signals indicative of temperature control desired for the heater/cooler 14, such signals being converted to a compatible analog mode for controlling the heater/cooler. Data interface 24 provides digital processing circuitry for developing the data represented by the graph shown in FIGS. 2 and 3, thereby providing an output in the form of a precise indication, such as a display of measured dew point or a corresponding output of measured relative humidity.

Figure 2:
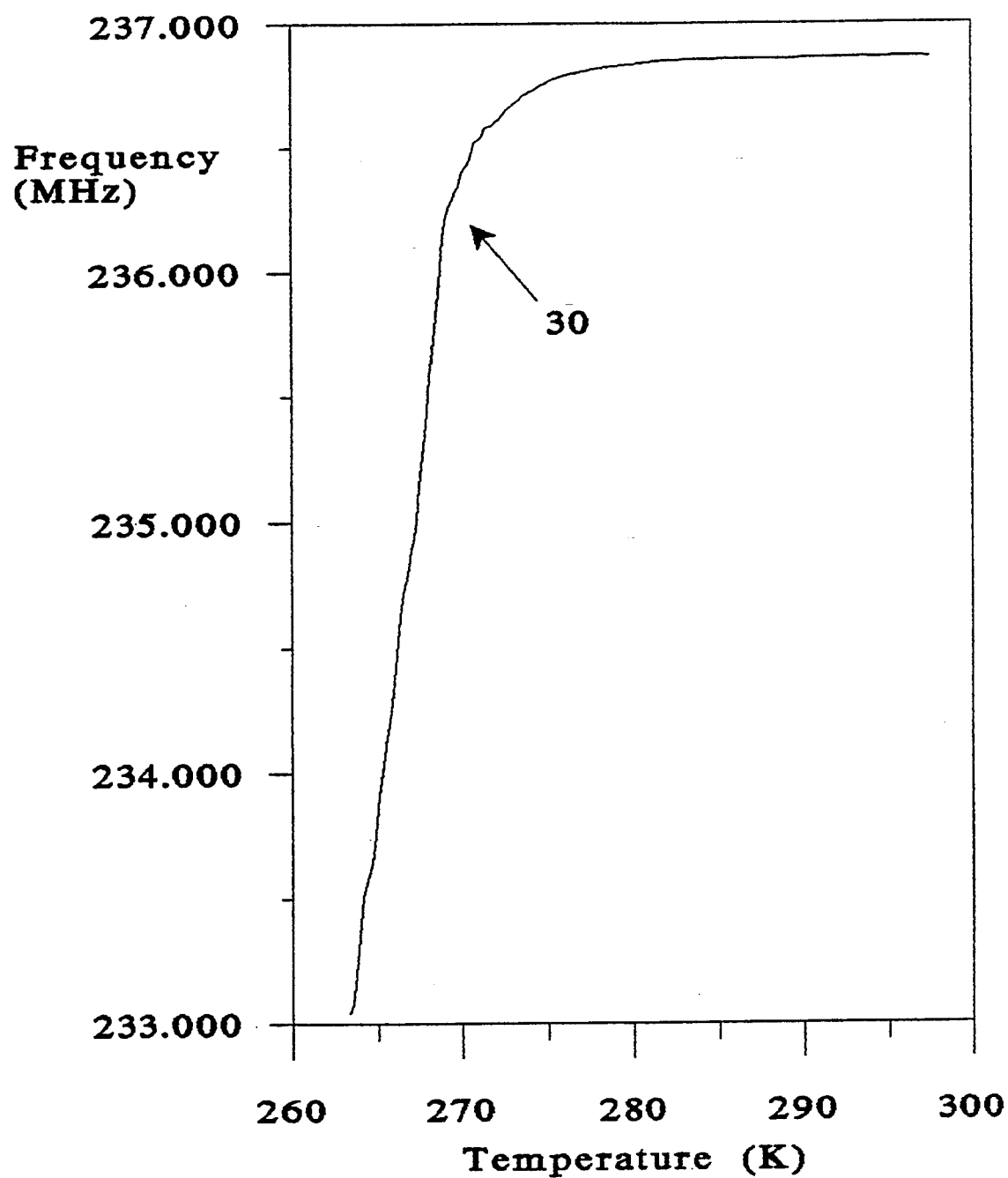
FIG. 2 is a graphical representation of signal vs. temperature used in the present invention to determine dew point.

Phenomena observed in the present invention and shown in the graph of IDT signal vs. temperature in FIG. 2, can be explained qualitatively by a description of the process of adsorption of water onto a polished glass surface. This process has been studied by H. Spencer-Gregory and E. Rourke in a book entitled Hygrometery, published by Pitman Publishing Company. This process is described in the aforementioned text in reference to a change in surface resistivity of a glass sample as the temperature is cooled through dew point. Of particular relevance is the data shown in FIG. 52, on page 102 of that text. As indicated therein, the formation of a water film onto the glass surface takes place in three stages.

The first stage exists at temperatures greater than about 9 degrees Centigrade above the dew point. Very little water exists on the surface in this region. The water layer is very thin and its structure is largely dominated by interactions with surface atoms of the substrate. In the case of the IDT sensor, there is a measureable, but relatively small change in signal, "S" as the sensor is cooled through this first stage. This occurs because the IDT is sensitive primarily to water loading and this loading increases very slightly as temperature is decreased in this region. As the temperature is decreased below approximately 9 degrees Centigrade above dew point, water formation enters the second stage which occurs between a temperature of 9 degrees Centigrade above dew point, down to dew point. At these temperatures, a uniform film of water is present on the surface and this film thickness increases as the temperature is reduced. This stage corresponds to a nearly logarithmic reduction in surface resistivity in the figure of Gregory and Rourke. In the case of the IDT the signal changes due to the increased water loading caused by cooling. As the film thickness is further increased, the role of substrate atoms in the energetics of the film becomes diminished and the film's character is largely governed by the film's surface energy (tension).

Figure 3:
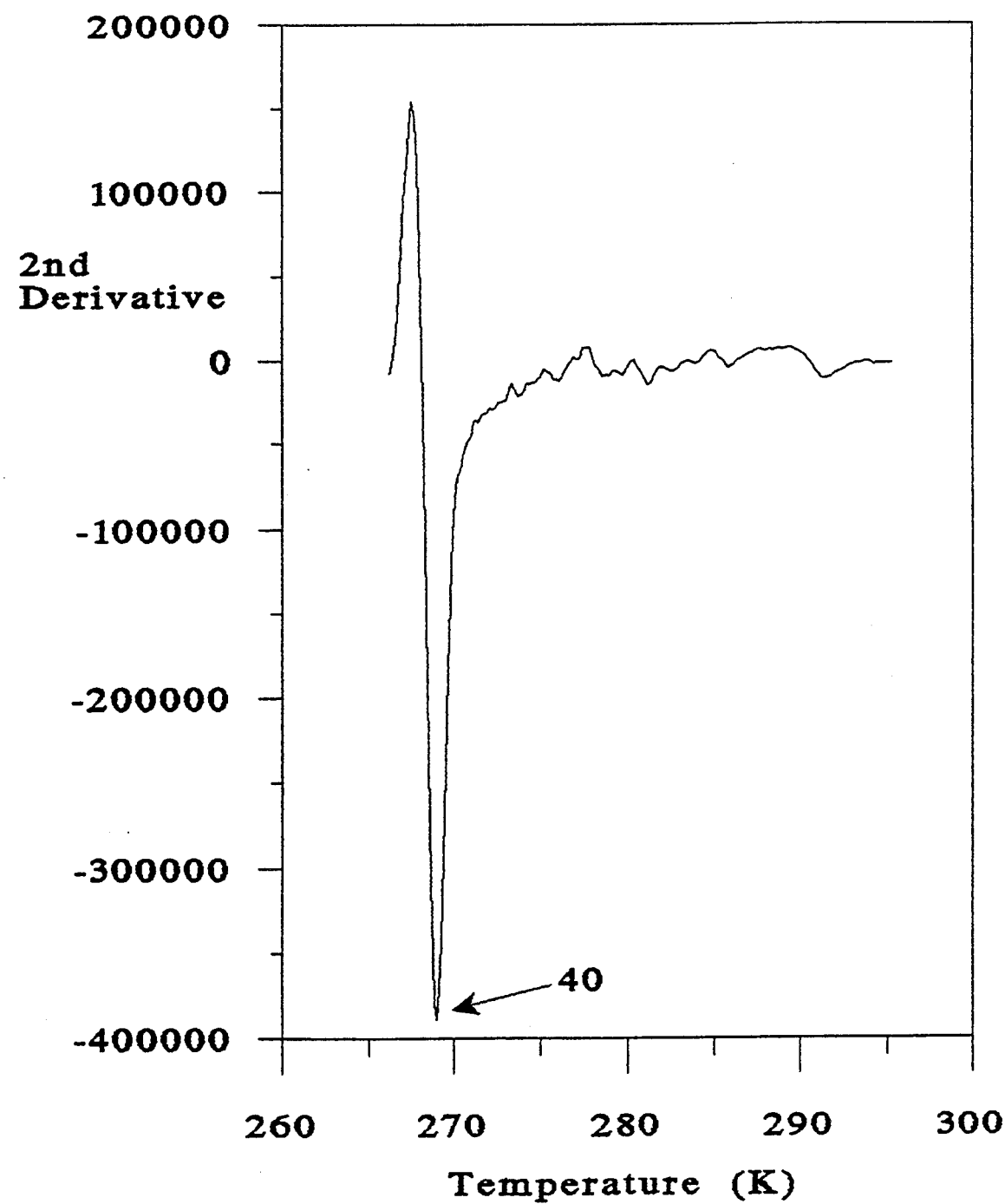
FIG. 3 is a graphical representation of the second derivative of the graph of FIG. 2, illustrating the precise dew point measurement capability of the present invention.

At the dew point, film formation enters its third stage and the film changes from a stable layer into fine droplets in order to minimize the surface energy of the system. These droplets are generally on the order of $10^{-5}$ centimeters in diameter. However, their exact size is governed by a large number of factors. Note that there is a critical film thickness at which the film rapidly breaks into droplets. This effect occurs rapidly (a very sharp feature) as temperature is lowered. As the temperature is further reduced, this droplet phase is replaced by a connected volume of liquid. The effect of droplet formation is a sharp increase in surface resistivity due to the discontinuous nature of the resulting layer. As the droplets coalesce back into a continuous film, the surface resistivity decreases. It is important to note that the water loading on the surface is not reduced at dew point, only the structure of the water layer changes at dew point. The IDT-based sensor response to this structural change with a clear shift in the rate the IDT signal is changed (i.e., change in slope or ds/dT). This feature 30 is noted in FIG. 2. However, because the IDT sensor is sensitive primarily to total water loading, it is expected that the IDT signal vs. temperature curve will change monotonically as temperature is lowered through dew point. This is because the water loading is not being reduced at dew point, only the rate is changing. The temperature at which the slope changes, provides an unambiguous measurement of dew point. Therefore plotting the second derivative of signal vs. temperature ($d^2s/dT^2$) allows this effect to be clearly seen as a peak at the dew point temperature 40 as shown in FIG. 3.

Having thus described a preferred embodiment of the invention, what is claimed is:

1. An apparatus for measuring dew point;
   the apparatus comprising:
   an interdigitated transducer configured for generating a moisture sensitive signal;
   a temperature-control device for varying the temperature at said transducer;
   a temperature sensor at said transducer for precisely monitoring the temperature adjacent a surface of said transducer;
   a signal detector connected to said transducer for monitoring a parameter of said signal;
   a controller means connected to said temperature-control device and to said detector for reducing the temperature at said transducer from a selected point above dew point to a selected point below dew point while concurrently monitoring said parameter of said signal;
   processing means for determining the second derivative of said parameter with respect to temperature of said transducer;
   an indicator means for reporting a measured dew point based upon an abrupt change in a variation of said, second derivative.

2. The apparatus recited in claim 1 wherein said temperature-control device comprises a cooler for lowering the temperature at said transducer and a heater for raising the temperature at said transducer.

3. The apparatus recited in claim 2 wherein said cooler lowers the temperature at said transducer from a point above dew point to a point below dew point wherein said heater raises the temperature at said transducer from said point below dew point to said point above dew point.

4. A method for measuring dew point comprising the steps of:
   a) providing an interdigitated transducer configured for generating a signal responsive to moisture;
   b) controlling the temperature at said transducer;
   c) measuring the temperature at said transducer;
   d) measuring a parameter of said signal while reducing the temperature at said transducer from a point above dew point to a point below dew point;
   e) measuring the second derivative of a variation of said parameter of said signal with respect to temperature at said transducer;
   f) reporting a measured dew point based upon an abrupt change in a variation of said second derivative of said variation of said parameter of said signal with respect to temperature at said transducer, and identifying the dew point as a temperature at which said abrupt change of said variation of said second derivative occurs.

5. The method recited in claim 4 wherein step d) comprises the step of starting said temperature reducing at a point above dew point and ending said temperature reducing at a point below dew point.

6. The method recited in claim 4 further comprising the step of heating said transducer after completing step f) for subsequently repeating said method.

* * * * *